(12) United States Patent
Didon (10) Patent No.: US 9,265,963 B2
(45) Date of Patent: Feb. 23, 2016

(54) DEFIBRILLATOR, RESCUE KIT OF PARTS AND PROCESS FOR CONTROLLING THE QUALITY OF CHEST COMPRESSION

(75) Inventor: Jean-Philippe Didon, Merkwiller-Pechelbronn (FR)

(73) Assignee: SCHILLER MEDICAL S.A.S., Wissembourg (FR)

( * ) Notice: Subject to any disclaimer, the term of this patent is extended or adjusted under 35 U.S.C. 154(b) by 507 days.

(21) Appl. No.: 12/720,751

(22) Filed: Mar. 10, 2010

(65) Prior Publication Data

US 2010/0234908 A1 Sep. 16, 2010

(30) Foreign Application Priority Data

Mar. 11, 2009 (EP) ..................................... 09154911

(51) Int. Cl.
*A61N 1/39* (2006.01)

(52) U.S. Cl.
CPC ................ *A61N 1/39* (2013.01); *A61N 1/3968* (2013.01); *A61N 1/3993* (2013.01)

(58) Field of Classification Search
CPC ..................... A61H 31/005; A61H 2201/5084; A61H 2201/5007; A61H 2230/04; A61H 2201/1253; A61H 2201/5061; A61H 2201/5071; A61H 2201/5079; A61H 2230/045; A61H 2230/06; A61H 31/007; A61H 2201/501; A61H 2201/5076; A61N 1/39; A61N 1/3925; A61N 1/3993; A61N 1/3625; A61N 1/3937; A61N 1/046; A61N 1/3968; A61B 5/11; A61B 2505/01; A61B 2562/0219; A61B 5/024; A61B 5/0402; G06F 19/3406; G06F 19/3481; G06F 19/34
USPC ................. 607/1–2, 5–6, 115, 142, 149, 152; 601/41; 434/265
See application file for complete search history.

(56) References Cited

U.S. PATENT DOCUMENTS

| | | | | |
|---|---|---|---|---|
| 6,827,695 | B2 * | 12/2004 | Palazzolo et al. | 601/41 |
| 7,220,235 | B2 * | 5/2007 | Geheb et al. | 601/41 |
| 2006/0270952 | A1 * | 11/2006 | Freeman et al. | 601/41 |
| 2008/0312709 | A1 | 12/2008 | Volpe | |

FOREIGN PATENT DOCUMENTS

| | | |
|---|---|---|
| EP | 1859770 | 11/2007 |
| WO | 01/56652 | 8/2001 |

* cited by examiner

*Primary Examiner* — Deborah Malamud
(74) *Attorney, Agent, or Firm* — Davis & Bujold PLLC; Michael J. Bujold (57) ABSTRACT

The invention relates to a defibrillator with integrated means for chest compression feedback. The defibrillator is shaped and sized such as to be directly placeable on the patient's chest.

12 Claims, 8 Drawing Sheets

DEFIBRILLATOR, RESCUE KIT OF PARTS AND PROCESS FOR CONTROLLING THE QUALITY OF CHEST COMPRESSION

The present invention relates to defibrillators, such as automated external defibrillators and public access defibrillators in particular, and rescue and emergency succour equipment kits and processes, according to the preambles of the independent claims.

Sudden Cardiac Arrest (SCA) is a medical emergency condition and a frequent consequence of a heart attack. During SCA the heart is no longer capable of sufficiently supplying the organism with blood as the normal blood flow is disrupted. Oxygen is thus prevented from reaching the organs, with various consequences, such as for example loss of consciousness. The longer the cardiac arrest goes untreated, the more likely it is to result in permanent damage, brain injury and ultimately death of the victim. The chance of survival decreases with time after the arrest.

It is thus paramount to provide medical attention to a SCA victim as quickly as possible. Treatment of cardiac arrest, which is associated with heart arrhythmias such as ventricular fibrillation (VF) or ventricular tachycardia, is performed with electric shocks. These defibrillation shocks are aimed at depolarizing a sufficient number of myocardial cells with the aim of allowing resumption of spontaneous rhythmic depolarization of the cells. The most important first aid measure for victims of cardiac arrest is Cardio Pulmonary Resuscitation (CPR). CPR is aimed at providing circulatory support until medical treatment such as defibrillation is available or a normal rhythm is spontaneously restored.

For a lay person with minimal or no training it is difficult to determine whether CPR is being performed correctly. Adequacy of frequency, depth and strength of the compressions need to be monitored to ensure that the victim does indeed benefit from these life support measures.

With increasing awareness of the time dependency on the survival chances of SCA victims, a growing number of public places and private institutions provide access to defibrillators. These public access defibrillators (PAD) have to be easily operable by lay persons with minimal or no training in life saving measures and be equally capable to perform all functions required by trained professionals. It has been found, that there is certain reluctance in the public for providing first aid measures to a SCA victim, a reluctance that is partially based on the fear of doing mistakes and possibly aggravating the victim's condition.

Therefore PADs come increasingly equipped with all kinds of support for the lay rescuer. One possibility is to prompt and provide guidance for the rescuer on the procedural steps.

The main focus should be to keep PADs for the lay rescuer easy to handle, reliable and safely operable. Thus reducing the emotional barrier for providing life saving first aid measures and increasing the quality of the succour thus provided is a desirable goal.

One easy way of aiding with chest compression is to use a metronome, for example a tact giving prompt integrated in the defibrillator or independent device, for providing the right frequency. There is no feedback on the chest compression quality though, as no measurements are taken on the compression itself.

Various solutions have been aimed at this goal so far. EP 1057451 A2 describes a system for measuring parameters of chest compression. It provides markings for the correct placement and can function as a stand alone device, connectable to a computer interface or as part of a defibrillator in the form of an additional pad to the two electrode pads. Chest compressions are analyzed using an accelerometer.

WO 2008/015624 A2 equally describes a chest compression coaching device with an internal sensor that is used as an independent further pad attachable to a defibrillator.

U.S. Pat. No. 6,125,299 depicts a force sensor for use in conjunction with an AED. The sensor measures a force applied to the sternum, compares it to a standard and feeds back prompts.

EP 1609453 A2 discloses a Cardio Pulmonary Reanimation (CPR) chest compression monitor that measures and prompts to facilitate administration of CPR. The hand held device can be attached to an ECG monitor or used as a stand alone device.

The entire prior art solutions are insufficient though. For lay persons the handling of an additional item in a stressful situation is disheartening, complicated and potentially dangerous. A total of up to four cable-connected items need to watched, made operational and eventually be placed on specific spots of the victim's chest, all the while the victim is in a critical state. The more items need to be operated, the higher the risk of wrong manipulation or confusion.

It is an object of the present invention to provide a solution to the problems of the state of the art. In particular, a system should be provided that has all the functionalities of an emergency kit for first aid with SCA and gives quality feedback and instructions to a rescuer reliably and is easily usable under distress by a lay rescuer, as well as a professional rescuer.

The problem is solved by a defibrillator, a process for controlling the quality of chest compression performance and a rescue kit of parts according to the characterizing portions of the independent patent claim.

One aspect of the present invention is a defibrillator with integrated means for chest compression feedback. The defibrillator is shaped and sized such as to be directly placeable on the patient's chest.

Means for chest compression feedback comprise at least a sensor element and an output means, such as, for example, a display.

Defibrillators are known in art as standard device for the treatment of ventricular fibrillation. Typically an output device is further provided for displaying the heart rhythm, allowing a medical care professional to determine whether a defibrillation shock is advised or not. If a defibrillator is capable of automatically diagnosing treatable rhythms it is called automatic external defibrillator (AED). Public access defibrillators (PAD) are AED, as they are most often required to be handled by lay rescuers.

A defibrillator usually comes with at least two electrode pads that are attached or placed on the patient's chest, usually in sternal-apical or even anterior-posterior placement. These electrodes are used for detecting ECG signals and administering a defibrillation shock. Electrode pads can be permanently attached to the housing of the defibrillator itself through connecting cables, be removable or integrated in the housing, depending on the form of the defibrillator.

In the light of the present invention means for integrated chest compression feedback is to be understood as a complex of detection/input, processing and outputting of information relating to the chest compression.

The means for integrated chest compression feedback used according to the invention can be any means that are capable of detecting chest compressions and convert hereby detected information into digital data for storage or output means. For example, a means of force detection can be included, that, upon exercising physical pressure, measures degree, acceleration, frequency, etc. of the force thus applied and converts said measurements into digital data, all the while analyzing for patterns. Alternative ways of detecting chest compression are equally feasible. For example, instead of force detection, the degree of chest compression itself can be measured by volume, or, in a further example, by measuring the distance between sternum and spine of the patient and deriving from the delta before and after compression said frequency and/or acceleration of compression. Further methods include the measurement of chest impedance. Methods for detecting and receiving data for feedback generation on chest compressions are known in the art.

In the device according to the invention, feedback can be provided by different means, such as visual representation through graphic displays, acoustic signals and/or voice prompts, tactile feedback and/or vibration, etc. or any combination thereof. Feedback can be provided on the basis of comparison of the input with device stored best practice standards, individually selectable standards, such as for example selecting prior to operation whether the patient is male, female, infant, etc. eventually also selecting age and estimated body mass. It would also be conceivable to apply individualized reference profiles for defibrillators that are used and kept at home by private households; or have the reference signal he directly transmitted on the AED by wireless technology or GPS. It would further be conceivable to have a prestored profile deposited in a data storage unit and/or on a personal identifying means, which, upon emergency, is inserted into a particular slot of the defibrillator, whereupon the applicable reference profile is downloaded/uploaded into/from the defibrillator's 1 processing unit.

Chest compression feedback routines can be adjusted and upgraded manually or digitally while the defibrillator is connected to a docking station in storage mode.

Chest compression routines might change as scientific research progresses. Currently AHA (American Heart Association) Guidelines for chest compression recommend lay rescuers with minimal or no training in cardiac resuscitation to apply a cheat compression only, so called hands-only CPR. Complete Guidelines and CPR protocols such as High-Frequency Chest Compressions, Open-Chest CPR, "Cough" CPR and Interposed Abdominal Compression CPR are explained by the AHA in Circulation (2005; 112:IV-47-IV-50).

With the importance of CPR for the survival rate of the victim being evident, it has still been found that there is reluctance in the public to succour an SCA victim. One of the main reasons is the fear to "do something wrong" and be overstrained with the situation.

By including the chest compression feedback means into the defibrillator and design the shape and size of the defibrillator in such a fashion that it can be directly placed on the patient's chest a significant burden of stress in the emergency situation is relieved from the operator. The rescuer is able to focus fully on the victim and his chest compression technique, all the while the defibrillator analyses the situation and the chest compression and gives supporting prompts and/or feedback to the rescuer.

Characteristic of this embodiment of the present invention is that the defibrillator is sized and shaped such as to be directly placeable on the patient's chest, meaning that there are limitations in weight and dimensions of the devise. The defibrillator is preferably not broader than 30 cm and not longer than 30 cm. Thickness can vary between the single elements, but should be generally kept as thin as possible in the regions that are not involved in chest compressions directly. The defibrillator might be essentially ergonomically formed to fit a anthropologically average human chest. The side of the defibrillator might consist a soft material and corners might be rounded, so as to confer a comfortable touch. It is further conceivable to shape the defibrillator such as to provide a maximum of force transmission from the rescuer's hands onto the sternum of the victim, while still carefully avoiding the concentration of the force into too small a point, so as to prevent injury.

In a particularly preferred embodiment the defibrillator is small enough, such as to cover little more than the rescuer's hands on the patient's chest. The rescuer could conceivably place such a "pocket defibrillator" on the patient's chest, attach the electrodes and apply the chest compressions while gripping the defibrillator.

Further advantages are the possibility to abstain in the defibrillator design from using a plurality of cables. Less cables and single devices that need to be watched and understood by the lay rescuer mean less uncertainty and an increased focus on life supporting measures. The housing of the defibrillator can be used directly as a chest compression aid. A further advantage is that the device, while resting on the patient's chest is always in the same field of vision of the rescuer as the patient, thus making visual prompts more efficient and less confusing.

In a further preferred embodiment the defibrillator is sized in length×width×height 30 cm×15 cm×15 cm, preferably less than 30 cm×less than 15 cm×less than 15 cm, even more preferred less than 25 cm×less than 8 cm×less than 9 cm. Preferably, the defibrillator is at least of a size that allows the rescuer place both hands on it, either side by side, or stacked.

In a preferred embodiment the defibrillator further comprises at least one area for placing the operators' hands on.

In one embodiment, the designated areas are hand rests with schematic pictures of the hand. Further conceivable would be an ergonomic and/or anatomical hand relief. Preferably the designated area is devised such as to be the optimal place for transferring the chest compression force from the device to the victim's thorax. The exact position for placing the rescuer's hands can be further aided by prompts issued by the device, lighting or special colours. It is highly advantageous to provide the rescuer with clear and concise operation steps. A clearly defined area for applying chest compression is useful for focusing on the task at hand. Furthermore the area can for example be preferably adapted to be the source of the chest compression detection and collects the data for analysis and feedback.

In a preferred embodiment said area comprises at least one handle.

It has been found that not all rescuers come equipped with the necessary strength for applying the correct chest compression force, or on the other hand, some rescuers might push too forceful and thus injure the victim further. It has been found that handles can be devised in a manner to be helpful for force transmission. In the most basic embodiment, a handle can, for example, comprise a protrusion from the defibrillator with an angular grip therefrom. The grip eases the handhold of the rescuer on the defibrillator and thus facilitates chest compressions. In more sophisticated embodiments, it could also be conceivable to include means for resistance and/or strengthening the force applied, such as for example levers.

It is furthermore preferable for a handle to be connected with the chest compression feedback, more precisely with the detector providing the data for chest compression feedback.

In a preferred embodiment the defibrillator further comprises means for detection of whether the defibrillator is in motion, particularly whether currently in use as an element for chest compression, or still, i.e. used for defibrillation only.

The rescuer is thus not required to instruct the defibrillator on whether used on the patient's chest, or as a standard (e.g. conventional) defibrillator.

Such means for detection of whether in motion or still could comprise inter alia, gyroscopes, balances, accelerometers, gravimeters, piezo elements, strain gauge etc.

In a preferred embodiment the defibrillator is adapted to be operated in at least a first mode of operation. The defibrillator is then in operation in a similar manner as a pad or pod for chest compression. The defibrillator further has at least a second mode of operation, wherein the defibrillator is operated as a conventional defibrillator.

In a preferred embodiment, a defibrillator is adapted to be used either as a chest compression device in addition to its standard functions, as well as a conventional defibrillator resting beside the victim while the rescuer performs first aid and/or life sustaining measures.

In the conventional defibrillator mode, the defibrillator analyzes ECG and determines shockability of rhythms as usual. Prompts are delivered to the rescuer relating to the rescue protocol and the presence of a shockable rhythm.

As a characteristic of said preferred embodiment, the defibrillator is placed on the chest of the patient. The operator places its hands on the defibrillator and performs chest compressions through the defibrillator onto the patient's chest. As a further characteristic of said preferred embodiment, the defibrillator recognizes autonomously that it is used as chest compression pad and initiates the first operation mode, where feedback on the chest compression is given to the operator. If the defibrillator is placed next to the patient, though, the defibrillator recognizes being still and initiates the second operation mode, whereby it performs all functions of a conventional defibrillator and delivering only the prompts adequate for said mode.

It is understood by a person skilled in the art, that a further characteristic of the present embodiment comprises means for the defibrillator to compare thresholds or characteristics of motion with predetermined standards, so as to prevent entering a wrong mode while being in motion, for example if operated inside a vehicle in motion.

In a preferred embodiment the defibrillator has means of automatically switching modes of operation depending on whether in motion or not.

To keep the interventions and preliminary manual operations required by the rescuer with the defibrillator as minimal and thus as easy as possible, it is highly advantageous the defibrillator be able to detect in which mode of operation it is currently used, and implement the respective procedure accordingly and independently. The defibrillator does, according to this particular embodiment, autonomously switch modes of operation.

In a preferred embodiment the defibrillator comprises means for prompting the operator with feedback relating to quality of CFR and/or ECG data analysis.

Means for prompting can be any means that can be outputted by the device. Such means can comprise, inter alia, voice prompts, sound, light, tactile prompts or any combination thereof. In a further preferred embodiment the language for verbal and/or voice prompts is selectable.

In a preferred embodiment at least the area for placing the operators' hands on is electrically insulated/shielded. In a further preferred embodiment the at least one handle is electrically insulated/shielded.

It has been found that it is advantageous to fabricate the elements that come into physical contact with the rescuer of electrically insulating material. Such material can be, inter alia, glass, Teflon or polyethylene, etc.

In a preferred embodiment, a part of the housing of the defibrillator is moveable or comprises moveable elements in order to facilitate chest compression.

The whole defibrillator can be used to apply the chest compression force onto the patient's chest. Alternatively, the housing can be built such as to comprise parts that are moveable against each other, in such a fashion as to allow the areas where the rescuer's hands are placed on, and the chest compression force is applied to, to transfer that force onto the patient's chest. The housing, or part of the housing, can thus either be constructed from an essentially flexible material, such as, for example, soft plastic, and/or comprise elements that allow for movement against each other. The defibrillator would thus consist of essentially two elements attached to each other in a moveable fashion. Bearings can be installed, for example, around the area where the hands of the operator are placed, so as to allow that area to move in respect to the rest of the defibrillator housing.

In one particular embodiment of the present invention the defibrillator takes the form of a blanket that can be placed on the patient's chest. The detection sensors are placed on the side that comes into contact with the chest, whereas the area that the operator's hands are placed upon points upward. Some elements of the defibrillator are solid for mandatory construction reasons, such as for example the energy source. These elements can be incorporated either in the moveable but solid area or placed in a non encumbering region of the defibrillator.

In a preferred embodiment the defibrillators' means for chest compression feedback are adapted for detecting quantitative and qualitative data on chest compression being performed on the patient.

In a preferred embodiment the defibrillators' means for chest compression feedback is a gyroscope, preferably said gyroscope is also the means for detection whether the defibrillator is in motion or not.

In an alternative embodiment the defibrillators' means for chest compression feedback is an accelerometer.

Accelerometers can be used to further act as detectors for whether the defibrillator is in motion or still. Piezoelements along horizontal and vertical axes can detect movement in any direction, thus it has been found that an accelerometer for chest compression detection can be used for detection of defibrillator motion.

A further aspect of the present invention is a process for controlling the quality of chest compressions performance with the steps of placing the defibrillator, on the chest of a patient, analyzing chest compression parameters with the defibrillator and delivering a prompt based on said analysis.

Another aspect of the present invention uses a defibrillator directly on a patient's chest for performing chest compression. Whereby said defibrillator has further means for analyzing chest compression and providing feedback, for example as prompts or LED signals.

An additional aspect of the present invention is a rescue kit of parts. Preferably said rescue kit of parts is in a transportable housing. In said rescue kit of parts at least the following elements are present: a chest placeable defibrillator, an energy source and a pair of electrodes. Preferably, said defibrillator has means for analyzing chest compression and providing feedback.

The energy source can be a transportable battery, for example incorporated into the transportable housing or the defibrillator itself, or, alternatively, can come from the grid by a plug connected by cable to a transformer or directly to the defibrillator. The transformer can form part of the transportable housing or be directly integrated into the defibrillator.

Alternatively it is further conceivable to have a rescue kit comprising a removable chest placeable AED connected by wire or through wirelessly communication with a housing element. Wherein said housing element further comprises a monitoring system. Said monitoring system or remote monitoring system is capable of displaying ECG, delivering prompts and CPR feedback. In a further embodiment, the housing element is transportable.

The invention will be further outlined in the following in reference to the preferred embodiments with examples and drawings.

Figure 1:
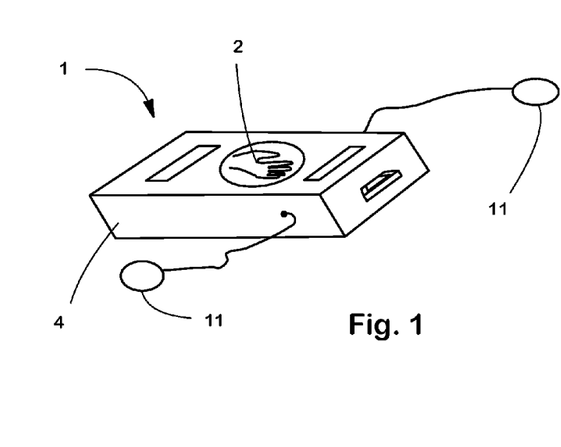
FIG. 1 shows a perspective and schematic drawing of a defibrillator according to a first embodiment of the invention.
Figure 2:
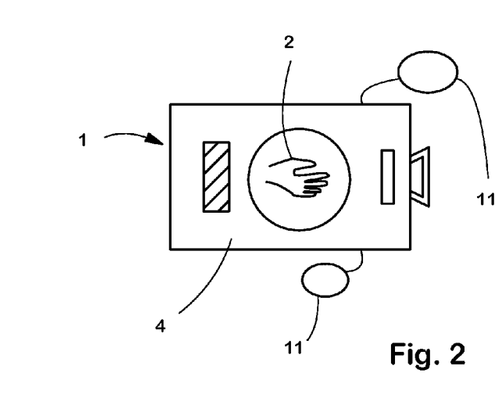
FIG. 2 shows a defibrillator according to a first embodiment of the invention in top view.
Figure 12:
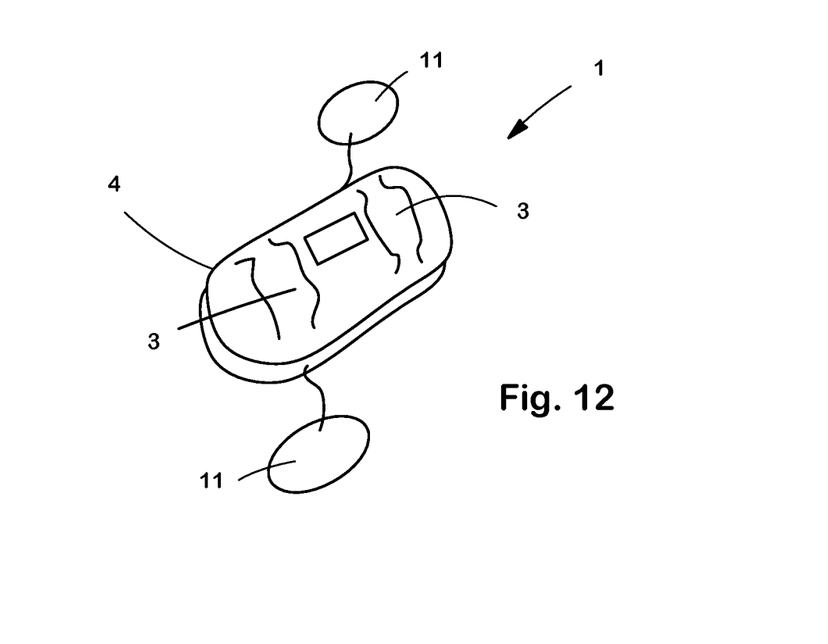
FIG. 12 shows a schematic drawing of a further particular embodiment of a defibrillator according to the invention.
Figure 13:
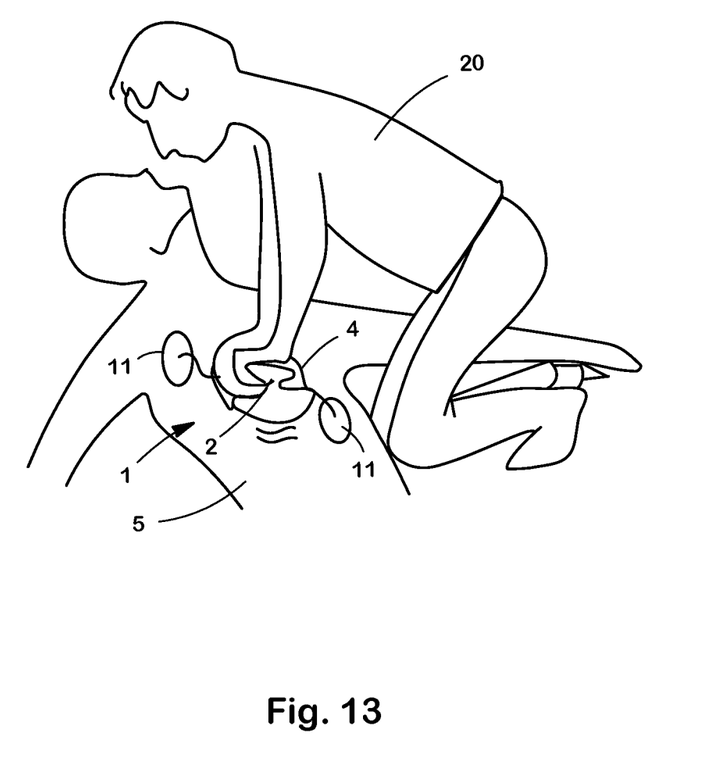

FIG. 13 shows a schematic drawing of the particular embodiment depicted in FIG. 12 during use FIGS. 1 and 2 are schematic drawings of a defibrillator 1 according to the invention. A defibrillator 1 housing 4 is sized and shaped such as to be placeable on the chest of a patient. This means, the defibrillator 1 housing 4 is smaller than 30 cm in width and smaller than 30 cm in length and from a lightweight material. The thickness of the defibrillator is 10 cm in the thickest part, such as the area 2, where the hands are placed, and 8 cm in the lowest part, the housing 4. The defibrillator 1 is further equipped with electrode pads 11 connected to the housing 4. Further the defibrillator has a clearly identifiable area 2, where the rescuer's hands are placed during administration of CPR. Said area 4 is insulated against electrical currents. In the present example, a polyethylene coating insulates the area 2 and the housing 4.

Figure 3:
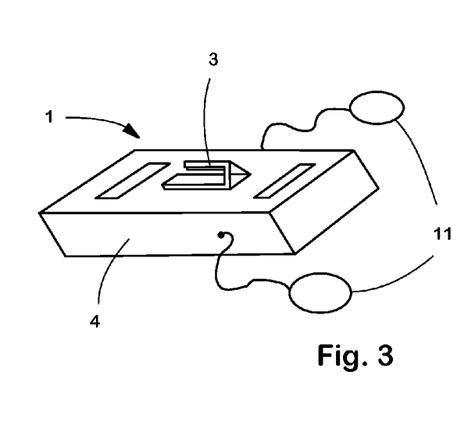
FIG. 3 shows a schematic perspective of a defibrillator according to another embodiment of the invention.

In FIG. 3 an example is shown, where the areas 2 shown in FIGS. 1 and 2 for placing the hands of the rescuer are replaced by a handle 3. Further elements of the defibrillator 1 are identical to the previously described examples with the electrode pads 11 and the housing 4.

Figure 4:
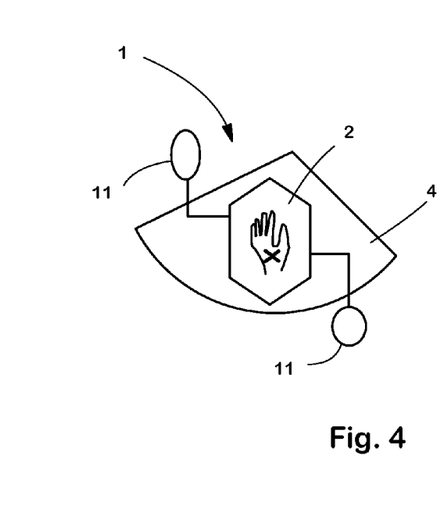
FIG. 4 shows a schematic representation of a further particular embodiment of a defibrillator according to the invention.

A specific example of a particular embodiment is shown in FIG. 4, where the housing 4 takes an essentially ergonomical shape and is constructed of an essentially foldable, soft material so as to be wrapped around the patient's chest for use. The defibrillator in the present example consists of a rubber blanket. The area 2' where the hands of the operator are placed on is clearly identified as such and provided with a reinforced shell 13 that aids in the transfer of the chest compression impulse onto the patient's thorax. The reinforced shell is made of polyethylene coated ceramic. In the concept example shown, the electrode pads 11 are partly sewn into the foldable housing, exiting the housing 4 where they are most conveniently attached to be attached to the torso.

Figure 5:
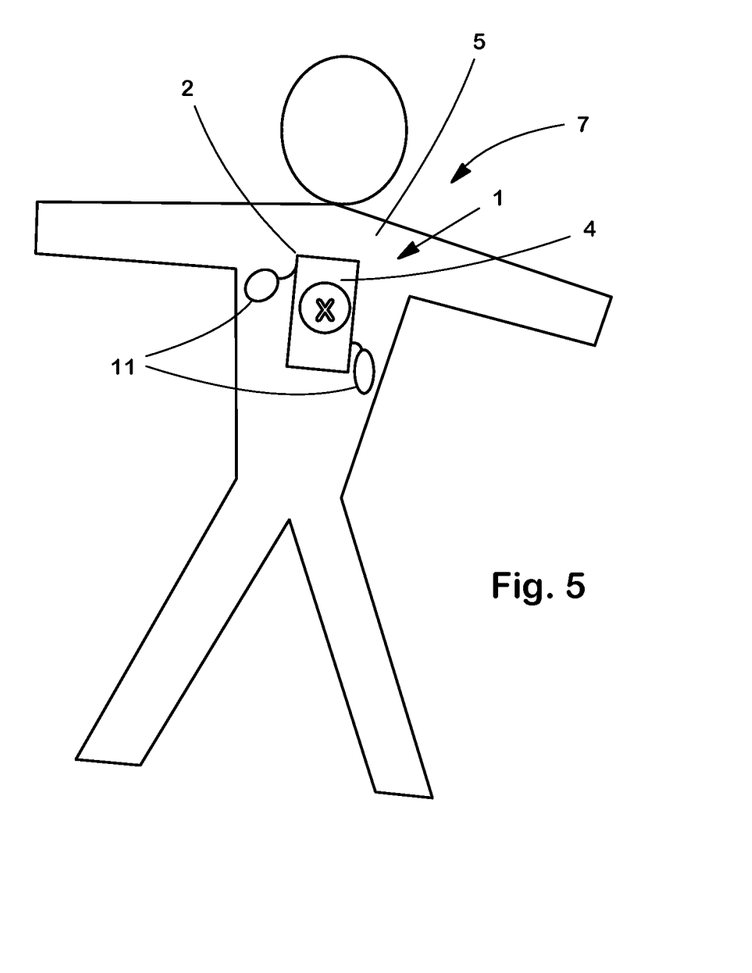
FIG. 5 shows a schematic drawing of an operative placement of the first embodiment of the defibrillator according to the invention on the chest of a patient in top view.

FIG. 5 is a schematic drawing depicting the placement, of the defibrillator 1 according to the invention on the chest 5 of the patient 7. The electrode pads 11, conventionally connected to the defibrillator 1 are placed in the respective position of the chest 5 for delivery of an adequate defibrillation shock. The area 2 where the chest compression is applied is marked on the defibrillator 1 on the housing 4. The position where the force is applied is in a straight line slightly below the nipples of the patient on the sternum.

Figure 6:
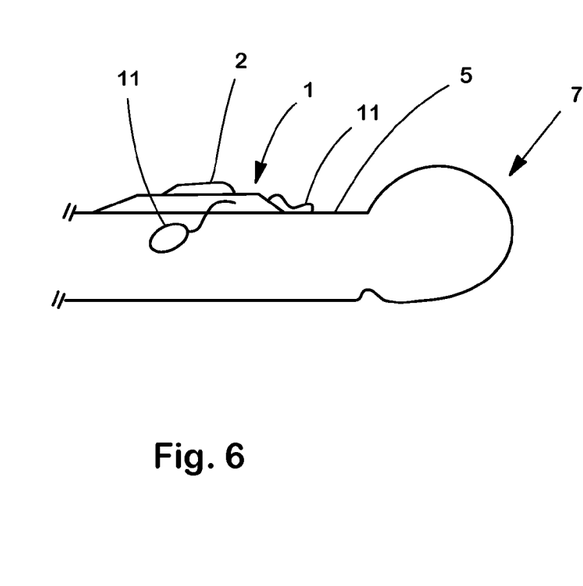
FIG. 6 shows a schematic drawing of the operative placement of the first embodiment of the defibrillator according to the invention on the chest of a patient in side view.

The same placement is shown in a schematic side view in FIG. 6, where the defibrillator 1 is placed on the patient's 7 chest 5, the electrode pads 11 are attached for example in the respective anterio-apical placement of external defibrillator electrodes on the chest 5. The area 2 where the operator's hands are placed on is further indicated, as well as the general chest compression movement axis indicated by arrows. This is the axis the pressure force for compression is applied to.

Figure 7:
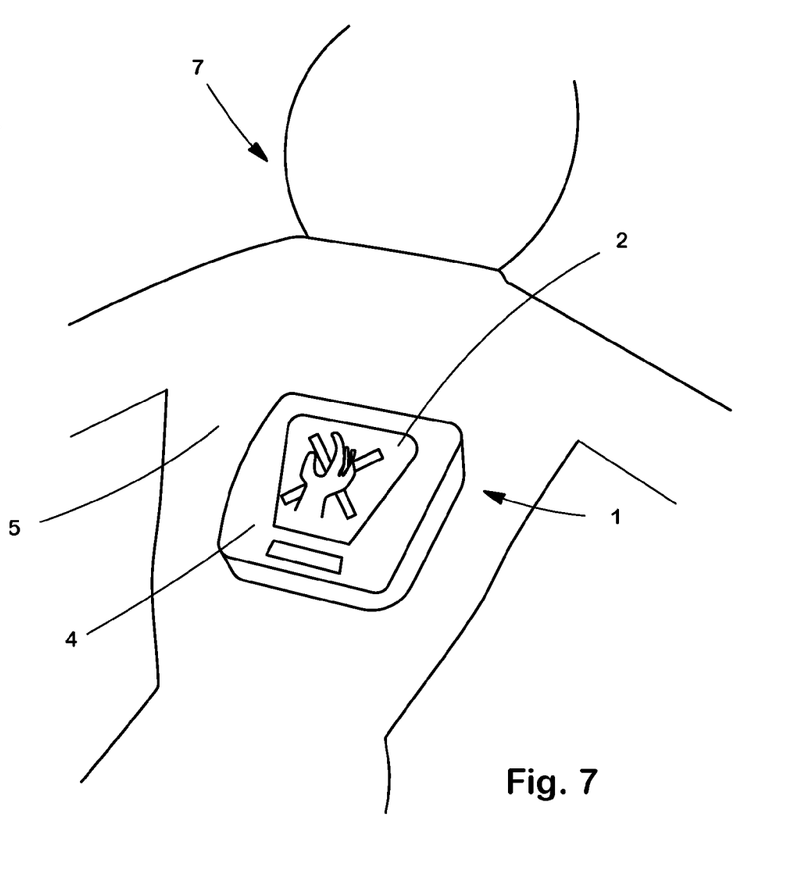
FIG. 7 shows a schematic drawing of the operative placement of an alternative embodiment of a defibrillator according to the invention on the chest of a patient in perspective view.

FIG. 7 shows an alternate defibrillator 1 placed on the chest 5 of a patient 7. The housing 4 of the defibrillator contains an area 2 that is signalled for placing the rescuer's hands on. A loudspeaker 14 prompts the rescuer on the steps that need to be performed during the emergency routine and provides feedback on quality of the chest compression and also on the presence of a shockable rhythm if such is found.

Figure 8:
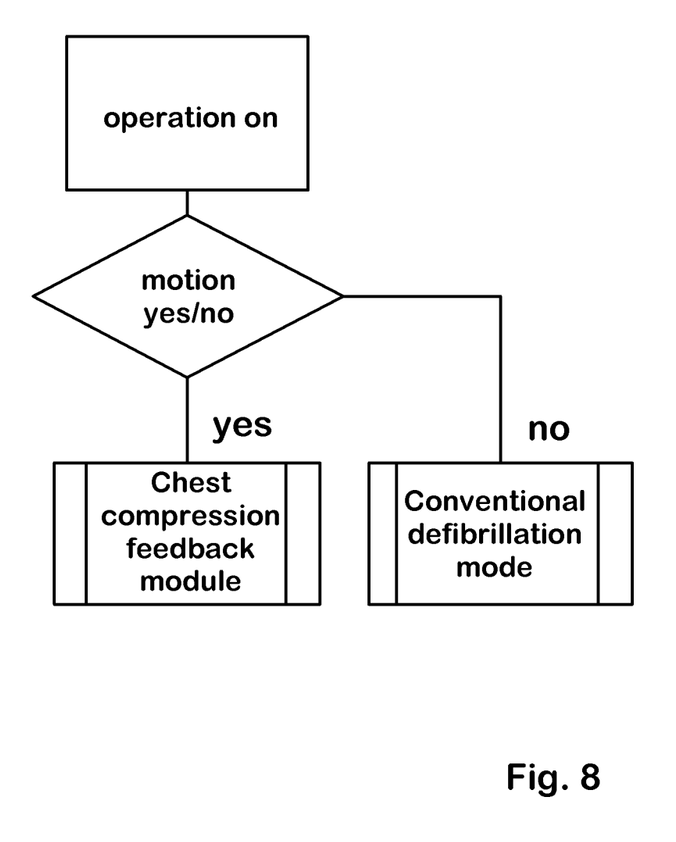
FIG. 8 shows a flowchart for an automatic decision pathway for alternating modes of operation.

In FIG. 8 an example for a simplified decision pathway is shown for the automated mode switch of a defibrillator. After assuming operation, the defibrillator's main processing unit receives feedback from a gyroscope on whether it is currently in motion or not. If the processing unit receives the information that it is currently still (motion no), it switches the mode to a conventional defibrillator mode, if, on the other hand, the defibrillator processor receives a signal that corresponds to a chest compression like motion (motion yes) it switches into chest compression feedback mode. The defibrillator is thus enabled to automatically prompt the rescuer with the right series of instructions and/or feedback. In the conventional defibrillator mode, the defibrillator analyzes ECG and determines shockability of rhythms as usual. Prompts are delivered to tale rescuer relating to the rescue protocol and the presence of a shockable rhythm.

Figure 9:
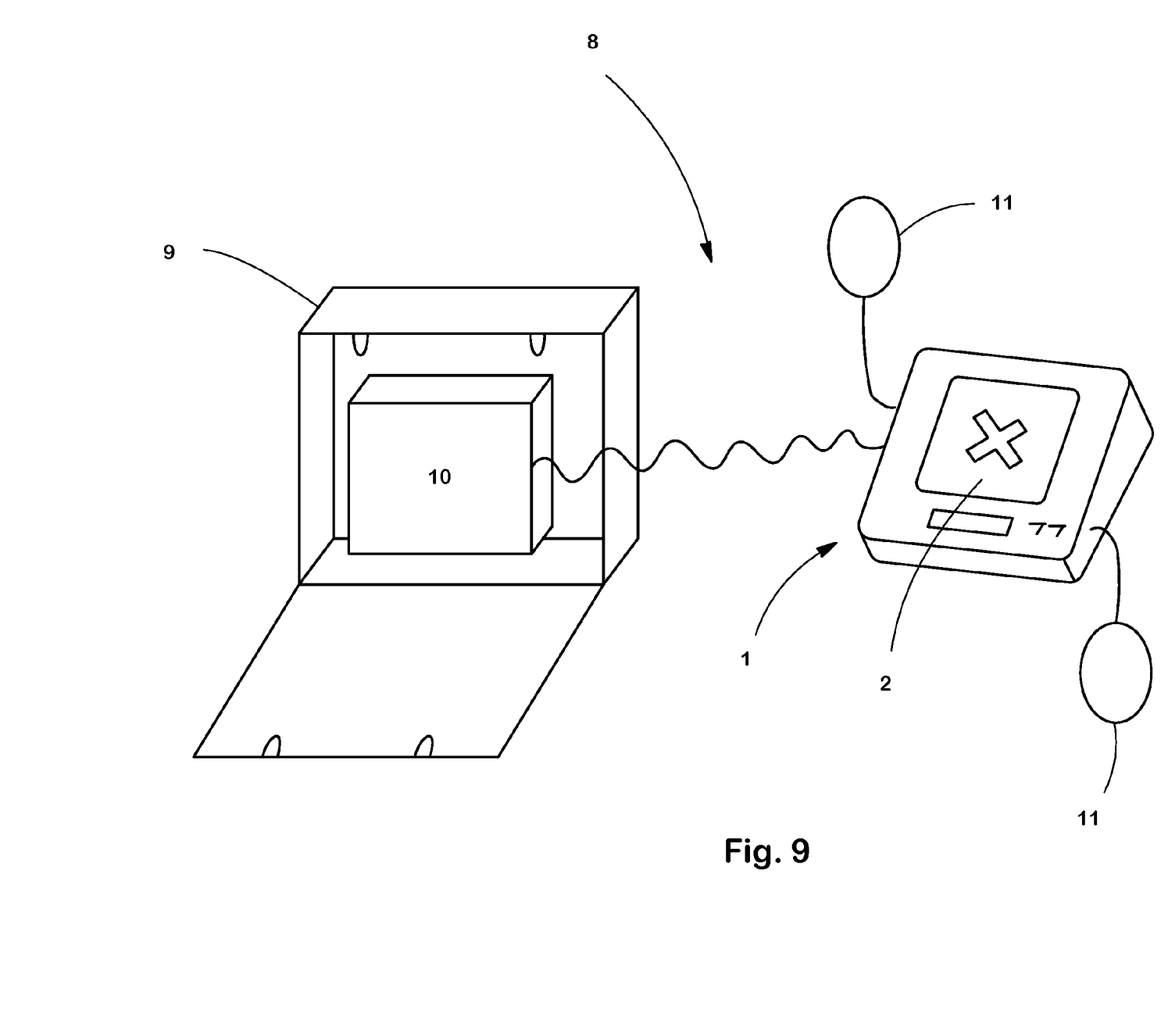
FIG. 9 shows a schematic drawing of an example rescue kit of parts according to the invention.

FIG. 9 shows a schematic arrangement for a rescue kit of parts 8 according to the invention. A transportable housing provides space for the defibrillator 1 with an indicated area 2 where the operator places his hands on during chest compression, the electrodes 11 and a battery pack 10. The battery is connected with the defibrillator 1 by an electrical cable 6.

Figure 10:
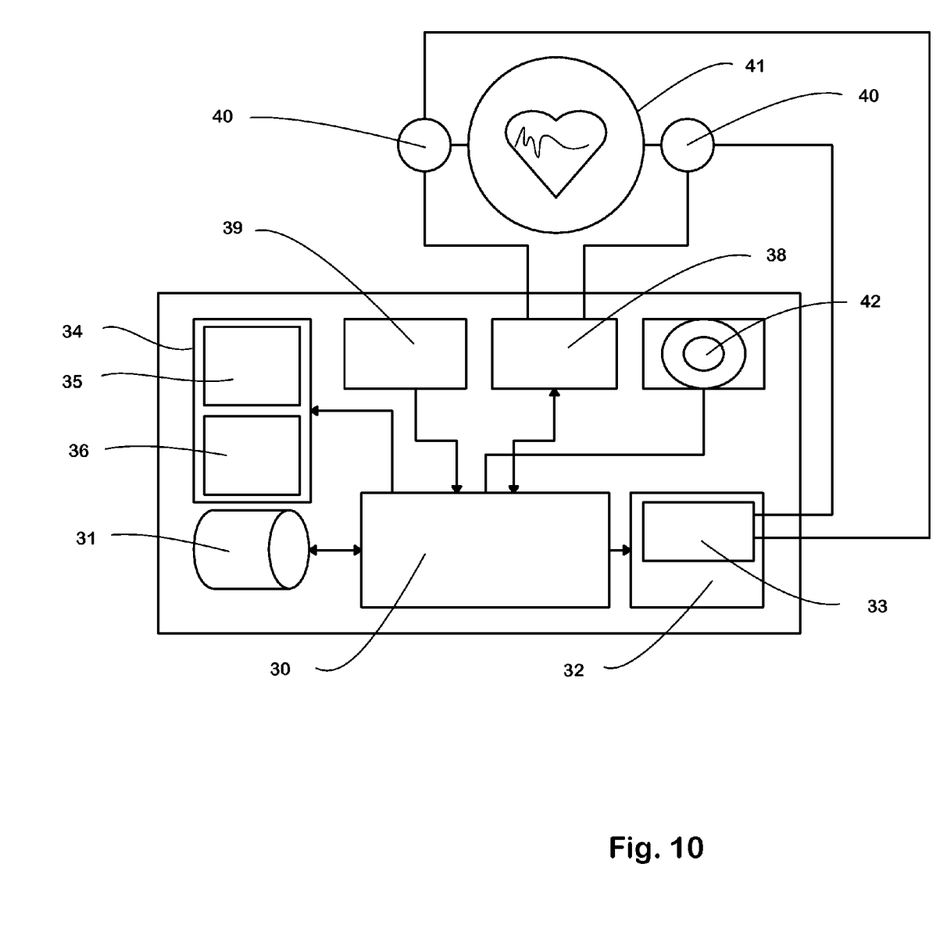
FIG. 10 shows a schematic overview of the defibrillator internal components according to the invention.

An example defibrillator or AED set up is shown in FIG. 10. An AED generally comprises an energy source 32 the circuitry for generating the defibrillation shock 33, such as a capacitor. An output unit 34 is further included, comprising an optical output monitor 35 and a voice prompt 36. The defibrillator further includes an ECG sensing circuit 38. Detection elements, such as electrode pads 40 are attached thereto. The user can interact with the machine through a user interface 39. During operation, a processor 30 is responsible for steering the various components according to the protocol and user input. The processor 30 is further capable of storing data or retrieving data from a data storage unit 31. During operation, the electrode pads 40 are attached to the patient's thorax 41 and function as sensors and shock delivery elements in the same time. A gyroscope 42 senses movement and provides information on whether the defibrillator is being used for chest compression to the processor 30. The processor 30 is further capable of changing mode of operation depending on the gyroscope 42 input. If the processor 30 determines from the input of the gyroscope 42 that the defibrillator is used as a chest compression pad, the processor analyzes the chest compression and issues commands to the output unit 34, which converts said commands to visual, or acoustic prompts through the output monitor 35 and the voice prompt 36, respectively.

Alternatively an accelerometer can be used instead of a gyroscope 42. Accelerometers are known in the art. Zoll's RED Plus uses CPR-pads which contain an accelerometer to measure the depth of CPR chest compressions, for example.

Figure 11:
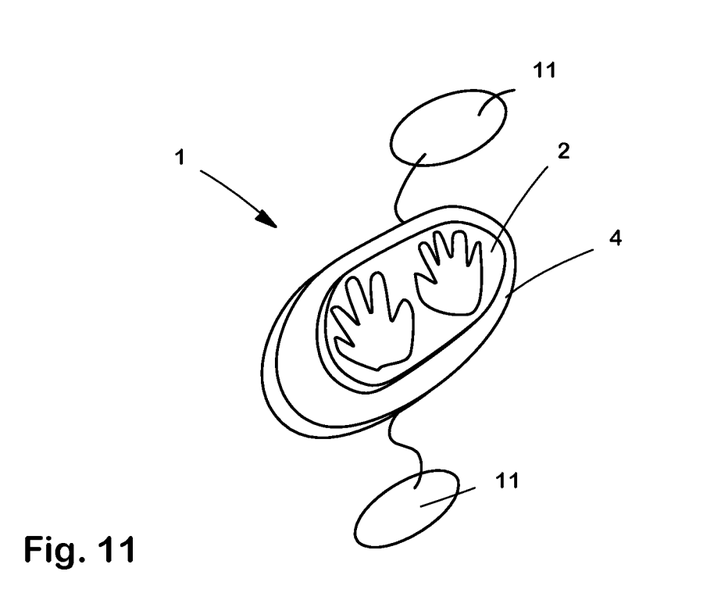
FIG. 11 shows a schematic drawing of a further particular embodiment of a defibrillator according to the invention.

In FIG. 11 an alternate defibrillator 1 according to the invention is shown. The housing 4 is ergonomically shaped and sized length 25 cm, width 8 cm and height 9 cm. The area 2 where the hands can be placed is shaped in such as fashion to allow resting both hands on the surface of the defibrillator 1.

FIG. 12 shows an additional alternate defibrillator 1 according to the invention. The housing 4 is designed as to provide two handles 3. The defibrillator is sized in length 23 cm, width 7.5 cm and height 9 cm.

FIG. 13 shows how the alternate defibrillator 1 of FIG. 12 is used during chest compression. The electrode pads 11 are placed on their respective position as recommended in the AHA Guidelines on the patient's chest 5. The rescuer 20 applies both hands on the handles 3 and applies the force through the housing 4 of the defibrillator 1 to the patient's chest 5.

I claim:

1. A defibrillator/chest compression aid, the defibrillator having a housing which is shaped and sized so as to be directly placeable on a chest of a patient,
   wherein said housing is directly usable as a chest compression aid,
   the said housing comprises at least one area for placing hands of an operator on,
   said area comprises at least one handle,
   said housing being shaped so as to provide a maximum of force transmission from the hands of the operator onto the chest of the patient,
   the defibrillator having means for chest compression feedback, said means being integrated in the defibrillator and adapted for detecting quantitative and qualitative data on a chest compression being performed on the patient, and the means for chest compression feedback being coupled to a processor which switches, if the feedback corresponds to a non-moving state, to a first mode of operation in which the defibrillator can be used directly for chest compression, and the processor switches, if the feedback corresponds to a moving state, to a second mode of operation in which the defibrillator can be used as a conventional defibrillator,
   the defibrillator having prompting elements for prompting a rescuer on steps that are needed to be performed during an emergency routine,
   the defibrillator comprises electrode pads, which are attached or attachable or integrated into said housing,
   the defibrillator further comprises means for detection of whether or not the defibrillator is in a moving state,
   the processor is adapted to receive feedback from said means on whether the defibrillator is in motion or not,
   the processor switches to a first mode of operation if the feedback corresponds to a moving state, and, in the first mode of operation, the defibrillator is used directly for chest compression and in which feedback on chest compression is given to the operator,
   the processor switches to a second mode of operation if the feedback corresponds to a non-moving state in which the defibrillator stands still, and, in the second mode of operation, the defibrillator is used as a conventional defibrillator, the defibrillator analyses ECG and determines shockability of rhythms and prompts are delivered to the operator relating to a rescue protocol and the presence of the shockable rhythm, and
   the processor automatically switches modes, between the first and the second mode of operation, depending on whether the defibrillator is in motion or not.

2. The defibrillator according to claim 1, wherein the defibrillator comprises means for prompting the operator with feedback relating to quality of CPR and/or ECG data analysis.

3. The defibrillator according to claim 1, wherein said one area for placing the operator's hands on is electrically insulated.

4. The defibrillator according to claim 1, wherein at least part of the housing is moveable or comprises moveable elements.

5. The defibrillator according to claim 1, wherein said means for chest compression feedback comprises a gyroscope.

6. The defibrillator according to claim 5, wherein the gyroscope detects whether the defibrillator is in motion or not.

7. The defibrillator according to claim 1, wherein said means for chest compression feedback comprises an accelerometer.

8. The defibrillator according to claim 7, wherein the accelerometer detects whether the defibrillator is in motion or not.

9. A process for controlling the quality of chest compressions performance, comprising the steps of placing a defibrillator according to claim 1, on the chest of a patient; analyzing chest compression parameters with the defibrillator and delivering a prompt based on said analysis.

10. A method for performing chest compression, wherein a defibrillator according to claim 1 is directly placed on a patient's chest.

11. A rescue kit of parts, preferably in a transportable housing, comprising:
   a chest placeable defibrillator according to claim 1;
   an energy source; and
   a pair of electrodes.

12. A defibrillator, the defibrillator having a housing being shaped and sized so as to be directly placeable on a chest of a patient, said housing of the defibrillator being directly usable as a chest compression aid,
   wherein said housing comprises at least one area for placing hands of an operator on,
   said at least one area for placing the hands of an operator on is electrically insulated and said housing is shaped so as to provide a maximum of force transmission from the hands of an operator onto the chest of the patient,
   the defibrillator having means for chest compression feedback, said means being integrated in the defibrillator and being adapted for detecting quantitative and qualitative data on chest compression being performed on the patient, and the means for chest compression feedback being coupled to a processor which switches, if the feedback corresponds to a non-moving state, to a first mode of operation in which the defibrillator can be used directly for chest compression, and the processor switches, if the feedback corresponds to a moving state, to a second mode of operation in which the defibrillator can be used as a conventional defibrillator, the defibrillator having prompting elements for prompting a rescuer on steps that are needed to be performed during an emergency routine, the defibrillator comprising electrode pads, which are attached to or attachable to or integrated into said housing of the defibrillator, the defibrillator further comprises means for detection of whether or not the defibrillator is in a moving state, the processor is adapted to receive feedback from said means on whether the defibrillator is in motion or not, depending upon the received feedback from said means on whether the defibrillator is in motion or not, the processor switching to a first mode of operation if the feedback corresponds to a moving state, and in the first mode of operation, the defibrillator is used directly for chest compression and in which feedback on chest compression is given to the operator; and the processor switching to a second mode of operation if the feedback corresponds to a non-moving state, in which the defibrillator stands still, and, in the second mode of operation, the defibrillator is used as a conventional defibrillator, the defibrillator analyses ECG and determines shockability of rhythms and prompts are delivered to the operator relating to a rescue protocol and a presence of the shockable rhythm, the processor automatically switching modes, between the first and the second mode of operation, depending on whether the defibrillator is in motion or not, and the defibrillator comprises means to compare thresholds or characteristics of motion, with predetermined standards, so as to prevent entering a wrong mode while being in motion.

* * * * *